(12) United States Patent
Bradley et al.

(10) Patent No.: US 7,759,508 B2
(45) Date of Patent: Jul. 20, 2010

(54) VOLATILE COPPER(1) COMPLEXES AND PROCESSES FOR DEPOSITION OF COPPER FILMS BY ATOMIC LAYER DEPOSITION

(75) Inventors: Alexander Zak Bradley, Drexel Hill, PA (US); Jeffery Scott Thompson, West Chester, PA (US); Kyung-Ho Park, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 481 days.

(21) Appl. No.: 11/858,431

(22) Filed: Sep. 20, 2007

(65) Prior Publication Data

US 2008/0063882 A1 Mar. 13, 2008

Related U.S. Application Data

(63) Continuation of application No. 10/903,060, filed on Jul. 30, 2004, now abandoned, which is a continuation-in-part of application No. 10/820,926, filed on Apr. 8, 2004, now abandoned.

(60) Provisional application No. 60/463,170, filed on Apr. 16, 2003.

(51) Int. Cl.
*C07F 1/08* (2006.01)
*B32B 15/04* (2006.01)
*C23C 16/00* (2006.01)

(52) U.S. Cl. ............... 556/12; 556/32; 556/110; 427/250; 427/337; 428/457

(58) Field of Classification Search .......... 556/32, 556/110, 12; 427/250, 337; 428/457
See application file for complete search history.

(56) References Cited

U.S. PATENT DOCUMENTS

| 5,464,666 | A | 11/1995 | Fine et al. |
|---|---|---|---|
| 5,820,664 | A | 10/1998 | Gardiner et al. |
| 6,372,918 | B1 | 4/2002 | Feustel et al. |
| 6,464,779 | B1 | 10/2002 | Akami et al. |
| 6,511,936 | B1 | 1/2003 | Kim et al. |
| 2001/0055877 | A1 | 12/2001 | Vaartstra |
| 2003/0135061 | A1 | 7/2003 | Norman et al. |
| 2003/0232142 | A1 | 12/2003 | Bradley et al. |

FOREIGN PATENT DOCUMENTS

| DE | 42 02 889 A1 | 8/1993 |
|---|---|---|
| WO | WO 2004/036624 A2 | 4/2004 |
| WO | WO 2004/046417 A2 | 6/2004 |

OTHER PUBLICATIONS

McGeachin et al., "Synthesis and properties of some B-diketimines derived from acetylacetone, and their metal complexes", Canadian Journal of Chemistry, 1968, pp. 1903-1912, vol. 46.
Ritala et al., "Atomic Layer Deposition", Handbook of Thin Film Materials, 2002, pp. 103-159.
Ogura, "Acetonitrile Complexes of Copper(I) Organosulfonates and Tetrafluoroborate", Transition Metal Chemistry, 1, 1976, pp. 179-182.
International Search Report in Parent International Application, published Nov. 4, 2004 as WO 2004/094589.

*Primary Examiner*—Porfirio Nazario Gonzalez

(57) ABSTRACT

Provided are novel 1,3-diimine copper complexes, and processes for using 1,3-diimine copper complexes in the deposition of copper on substrates, or in or on porous solids, by atomic layer deposition.

12 Claims, No Drawings

VOLATILE COPPER(1) COMPLEXES AND PROCESSES FOR DEPOSITION OF COPPER FILMS BY ATOMIC LAYER DEPOSITION

REFERENCE TO RELATED APPLICATIONS

This is a continuation of U.S. patent application Ser. No. 10/903,060, filed on Jul. 30, 2004, which was a continuation-in-part of U.S. patent application Ser. No. 10/820,926, filed on Apr. 8, 2004, now abandoned.

FIELD OF THE INVENTION

The present invention relates to processes for the deposition of copper on substrates or in or on porous solids in an atomic layer deposition process. The processes use novel 1,3-diimine copper complexes and the use of 1,3-diimine copper complexes.

TECHNICAL BACKGROUND

Atomic layer deposition (ALD) processes are useful for the creation of thin films, as described by M. Ritala and M. Leskela in "Atomic Layer Deposition" in *Handbook of Thin Film Materials*, H. S. Nalwa, Editor, Academic Press, San Diego, 2001, Volume 1, Chapter 2. Such films, especially metal and metal oxide films, are critical components in the manufacture of electronic circuits and devices.

In an ALD process for depositing copper films, a copper precursor and a reducing agent are alternatively introduced into a reaction chamber. After the copper precursor is introduced into the reaction chamber and allowed to adsorb onto a substrate, the excess (unadsorbed) precursor vapor is pumped or purged from the chamber. This process is followed by introduction of a reducing agent that reacts with the copper precursor on the substrate surface to form copper metal and a free form of the ligand. This cycle can be repeated if needed to achieve the desired film thickness.

ALD differs from chemical vapor deposition (CVD) in the decomposition chemistry of the metal complex. In a CVD process, the complex undergoes pyrolytic decomposition on contact with the surface to give the desired film. In an ALD process, the complex is not completely decomposed to metal on contact with the surface. Rather, formation of the metal film takes place on introduction of a second reagent, which reacts with the deposited metal complex. In the preparation of a copper film from a copper(I) complex, the second reagent is a reducing agent. Advantages of an ALD process include the ability to control the film thickness and improved conformality of coverage because of the self-limiting adsorption of the precursor to the substrate surface in the first step of the process.

Ligands for use in ALD processes are stable with respect to decomposition and be able to desorb from the complex in a metal-free form. Following reduction of the copper, the ligand is liberated and removed from the surface to prevent its incorporation into the metal layer being formed.

S. G. McGeachin, *Canadian Journal of Chemistry*, 46, 1903-1912 (1968), discloses the synthesis of 1,3-diimines and metal complexes of thereof, including bis-chelate or homoleptic complexes of the form $ML_2$.

U.S. Pat. No. 6,464,779 discloses a Cu atomic layer CVD process that requires treatment of a copper precursor containing both oxygen and fluorine with an oxidizing agent to form copper oxide, followed by treatment of the surface with a reducing agent.

WO 2004/036624 discloses a two-step ALD process for forming copper layers comprising forming a copper oxide layer from a non-fluorine containing copper precursor on a substrate and reducing the copper oxide layer to form a copper layer on the substrate. Copper alkoxides, copper β-diketonates and copper dialkylamides are preferred copper precursors. The reducing agent is a hydrogen ($H_2$) containing gas.

US 2003/0135061 discloses a dimeric copper(I) precursor which can be used to deposit metal or metal-containing films on a substrate under ALD or CVD conditions.

WO 2004/046417 discloses the use of dimeric copper (I) complexes comprising amidinate ligands for use in an ALD process.

SUMMARY OF THE INVENTION

One aspect of the present invention is a copper complex, (I),

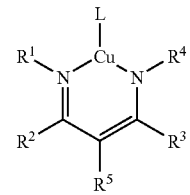

(I)

wherein

L is selected from the group consisting of $C_2$-$C_{15}$ olefins, $C_2$-$C_{15}$ alkynes, and aromatic heterocycles;

$R^1$ and $R^4$ are the same and are selected from the group consisting of H, isobutyl, and neopentyl; or $R^1$ is isobutyl and $R^4$ is methyl, ethyl, isopropyl or neopentyl; or $R^1$ is neopentyl and $R^4$ is isopropyl;

$R^2$ and $R^3$ are independently methyl or ethyl;

$R^5$ is H.

Another aspect of the invention is a process for forming copper deposits on a substrate comprising:

a. contacting a substrate with a copper complex, (I), to form a deposit of a copper complex on the substrate; and

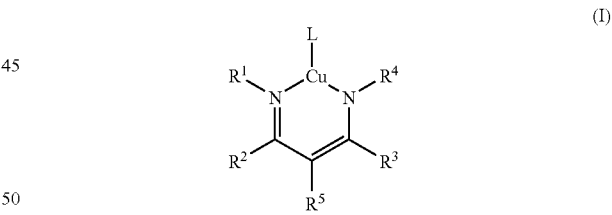

(I)

b. contacting the deposited copper complex with a reducing agent, wherein

L is selected from the group consisting of $C_2$-$C_{15}$ olefins, $C_2$-$C_{15}$ alkynes, and aromatic heterocycles;

$R^1$ and $R^4$ are the same and are selected from the group consisting of H, isobutyl, and neopentyl; or $R^1$ is isobutyl and $R^4$ is methyl, ethyl, isopropyl or neopentyl; or $R^1$ is neopentyl and $R^4$ is isopropyl;

$R^2$ and $R^3$ are independently methyl or ethyl;

$R^5$ is H; and the reducing agent is selected from the group consisting of 9-BBN (9-borabicyclo[3.3.1]nonane); diborane; boranes of the form $BR_xH_{3-x}$, where x=0, 1 or 2, and R is independently selected from the group consisting of phenyl and $C_1$-$C_{10}$ alkyl groups; dihydrobenzofuran; pyrazoline; disilane; silanes of the form $SiR'_yH_{4-y}$, where y=0, 1, 2 or 3, and R' is independently selected from the group consisting of phenyl and $C_1$-$C_{10}$ alkyl groups; and germanes of the form $GeR''_zH_{4-z}$, where z=0, 1, 2, or 3, and R" is independently selected from the group consisting of phenyl and $C_1$-$C_{10}$ alkyl groups.

DETAILED DESCRIPTION

Applicants have discovered an atomic layer deposition (ALD) process suitable for creation of copper films for use as seed layers in the formation of copper interconnects in integrated circuits, or for use in decorative or catalytic applications. The process uses copper(I) complexes that are volatile, thermally stable and derived from ligands that contain C, H, Si and N, but are not limited to these elements. "Volatile", as used herein, means that a material sublimes or evaporates without decomposition at moderate temperatures. In the present disclosure, "moderate temperatures" is used in a conventional sense, and generally means temperatures ranging from slightly above room temperature to about 200° C. "Thermally stable" means that the material does not decompose at the temperature of interest, generally about 100-200° C.

The ligands are chosen to form copper(I) complexes that are volatile in an appropriate temperature range but do not decompose to copper metal in this temperature range; rather, the complexes decompose to metal on addition of a suitable reducing agent. The ligands are further chosen so that they will desorb without decomposition upon exposure of the copper complex to a reducing agent. The reduction of these copper complexes to copper metal by readily available reducing agents has been demonstrated to proceed cleanly at moderate temperatures. As used herein, the term "cleanly" refers to preferred embodiments in which the only non-volatile species formed is copper.

In the process disclosed herein, copper is deposited on a substrate by:

a. contacting a substrate with a copper complex, (I), to form a deposit of a copper complex on the substrate; and

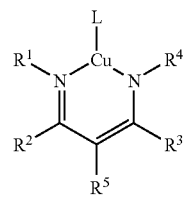

(I)

b. contacting the deposited copper complex with a reducing agent, wherein

L is selected from the group consisting of $C_2$-$C_{15}$ olefins, $C_2$-$C_{15}$ alkynes, and aromatic heterocycles;

$R^1$ and $R^4$ are the same and are selected from the group consisting of H, isobutyl, and neopentyl; or $R^1$ is isobutyl and $R^4$ is methyl, ethyl, isopropyl or neopentyl; or $R^1$ is neopentyl and $R^4$ is isopropyl;

$R^2$ and $R^3$ are independently methyl or ethyl;

$R^5$ is H; and the reducing agent is selected from the group consisting of 9-BBN; diborane; boranes of the form $BR_xH_{3-x}$, where x=0, 1 or 2, and R is independently selected from the group consisting of phenyl and $C_1$-$C_{10}$ alkyl groups; dihydrobenzofuran; pyrazoline; disilane; silanes of the form $SiR'_yH_{4-y}$, where y=0, 1, 2 or 3, and R' is independently selected from the group consisting of phenyl and $C_1$-$C_{10}$ alkyl groups; and germanes of the form $GeR''_zH_{4-z}$, where z=0, 1, 2, or 3, and R" is independently selected from the group consisting of phenyl and $C_1$-$C_{10}$ alkyl groups.

The deposition processes disclosed herein differ from prior processes of the art by allowing the use of lower temperatures and producing higher quality, more uniform films. The processes also provide a more direct route to a copper film, avoiding the formation of an intermediate oxide film.

The copper can be deposited on the surface, or in or on porosity, of the substrate. Suitable substrates include conducting, semiconducting and insulating substrates, including copper, silicon wafers, wafers used in the manufacture of ultra large scale integrated circuits, wafers prepared with dielectric material having a lower dielectric constant than silicon dioxide, and silicon dioxide and low k substrates coated with a barrier layer. "Low k" refers to a material with a small dielectric constant relative to that of silicon dioxide. Barrier layers to prevent the migration of copper include tantalum, tantalum nitride, titanium, titanium nitride, tantalum silicon nitride, titanium silicon nitride, tantalum carbon nitride, and niobium nitride.

The process can be conducted in solution, i.e., by contacting a solution of the copper complex with the reducing agent. However, it is preferred to expose the substrate to a vapor of the copper complex, and then remove any excess copper complex (i.e., undeposited complex) by vacuum or purging before exposing the deposited complex to a vapor of the reducing agent. After reduction of the copper complex, the free form of the ligand can be removed via vacuum, purging, heating, rinsing with a suitable solvent, or a combination of such steps.

The process can be repeated to build up thicker layers of copper, or to eliminate pin-holes.

The deposition of the copper complex is typically conducted at 0 to 200° C. The reduction of the copper complex is typically carried out at similar temperatures, 0 to 200° C.

Initially, a copper complex is deposited on the substrate. The formation of a metallic copper film does not occur until the copper complex is exposed to the reducing agent.

Aggressive reducing agents are used to reduce the copper complex rapidly and completely. Desirable reducing agents are volatile and do not decompose on heating, and are of sufficient reducing power to react rapidly on contact with the copper complex deposited on the substrate surface. A group of suitable reducing agents has been identified that have been used for copper(I) reduction in an ALD process. One feature of the reducing agents is the presence of a proton donor. The reducing agent is able to transfer at least one electron to reduce the copper ion of the complex and at least one proton to protonate the ligand. The oxidized reducing agent and the protonated ligand can then be removed from the surface of the newly formed copper deposit. Suitable reducing agents include 9-BBN, borane, diborane, dihydrobenzofuran, pyrazoline, germanes, diethylsilane, dimethylsilane, ethylsilane, phenylsilane, silane and disilane. Diethylsilane and silane are preferred.

In one embodiment of the copper deposition process, the copper complexes are added to a reactor under conditions of temperature, time and pressure to attain a suitable fluence of complex to the surface of the substrate. One of skill in the art will appreciate that the selection of these variables will depend on chamber and system design, and the desired process rate. After at least a portion of the copper complex has been deposited on the substrate (e.g., a coated silicon wafer), the undeposited complex vapor is pumped or purged from the chamber and the reducing agent is introduced into the chamber at a pressure of approximately 50 to 760 mTorr to reduce the adsorbed copper complex. The substrate is held at a temperature between approximately 0 to 200° C. during reduction. With suitable combinations of copper complex and reducing agent, this reduction is rapid and complete. Reducing agent exposure times can be from less than a second to several minutes. It is important that the products from this reaction are readily removed from the surface of the substrate under the reducing conditions.

In one embodiment, the copper complex is a copper 1,3-diimine complex (I), wherein $R^1$ and $R^4$ are isobutyl groups, $R^2$ and $R^3$ are methyl groups, and L=vinyltrimethylsilane, and the reducing agent is diethylsilane.

This invention also provides novel 1,3-diimine copper complexes, (I),

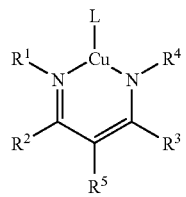

(I)

wherein

L is selected from the group of $C_2$-$C_{15}$ olefins, $C_2$-$C_{15}$ alkynes, and aromatic heterocycles;

$R^1$ and $R^4$ are the same and are selected from the group consisting of H, isobutyl, and neopentyl; or $R^1$ is isobutyl and $R^4$ is methyl, ethyl, isopropyl or neopentyl; or $R^1$ is neopentyl and $R^4$ is isopropyl;

$R^2$ and $R^3$ are independently methyl or ethyl;

$R^5$ is H.

In one embodiment, L is a linear, terminal olefin. For olefins of 4-15 carbons, L can also be an internal olefin of cis- or trans-configuration; cis- is preferred. L can be a cyclic or bicyclic olefin. L can also be substituted, for example with fluorine or silyl groups. Suitable olefins include, but are not limited to vinyltrimethylsilane, allyltrimethylsilane, 1-hexene, 4-methyl-1-pentene, 3,3-dimethyl-1-butene, and norbornene. L can also be alkyne or an aromatic nitrogen heterocycle such as pyridine, pyrazine, triazine, and N-substituted imidazole, pyrazole, and triazole.

In another embodiment, this invention provides an article comprising 1,3-diimine copper complexes, (I), deposited on a substrate. Suitable substrates include: copper, silicon wafers, wafers used in the manufacture of ultra-large scale integrated circuits, wafers prepared with dielectric material having a lower dielectric constant than silicon dioxide, and silicon dioxide and low k substrates coated with a barrier layer. Barrier layers can be used to prevent the migration of copper. Suitable barrier layers include: tantalum, tantalum nitride, titanium, titanium nitride, tantalum silicon nitride, titanium silicon nitride, tantalum carbon nitride, and niobium nitride.

EXAMPLES

Unless otherwise stated, all organic reagents are available from Sigma-Aldrich Corporation (Milwaukee, Wis., USA). The (2-amino)heptafluoro-4-imino-2-pentene was obtained from Matrix Scientific (Columbia, S.C., USA). The [Cu(CH$_3$CN)$_4$]SO$_3$CF$_3$ can be prepared according to the method described in: T. Ogura, Transition Metal Chemistry, 1, 179-182 (976).

Example 1

Preparation and Reduction of Vinyltrimethylsilane (N,N'-diisobutyl-2,4-pentanediketiminate)copper In a dry box under a nitrogen atmosphere, a 250 mL round-bottom flask was charged with 4-(isobutylamino)-3-pentene-2-one (36.9 g, 237 mmole) and dimethylsulfate (30.0 g, 237 mmole). The reaction solution was stirred for 5 minutes and then allowed to stand without stirring overnight. The yellow mixture became orange and viscous. Isobutyl amine (18 g, 246 mmole) was added with vigorous stirring via addition funnel. The solution was stirred for one hour until it solidified. The intermediate salt was not isolated, but was directly converted to the free amine (based on the theoretical yield of the intermediate salt) as described below.

A solution of NaOMe (12.8 g, 237 mmole) in MeOH (ca 40 mL) was added to the intermediate salt and stirred for one hour. The solvent was removed under vacuum to give a yellow oil that was extracted with pentane, filtered, and concentrated to give a yellow oil that consisted of the desired product (N,N'-diisobutyl-2,4-pentanediketimine) (ca 75%) and unreacted starting material (ca 25%) based on proton NMR data. The product was isolated by fractional distillation to give a yellow oil (35.4 g, 72% yield).

In the dry box, a 100-mL round-bottom flask was charged with [Cu(CH$_3$CN)$_4$]SO$_3$CF$_3$ (1.0 g), vinyltrimethylsilane (26.0 mmole), and diethyl ether (20 mL). In a separate 100-mL round-bottom flask, 1.5 M t-butyl lithium (1.7 mL) was added to a solution of N,N'-diisobutyl-2,4-pentanediketimine (0.550 g), prepared as described above. After 0.5 h, the solutions were combined. The combined solution changed from a cloudy white suspension to a golden-brown, clear solution after the uptake of all solids. After 2 h, the solution was concentrated to a solid/sludge, extracted with pentane (3×15 mL), filtered and concentrated to give a viscous oil (0.600 g, 62% yield).

Other ligands can be prepared similarly from analogous amino ketones.

Example 2

The viscous oil isolated as the final product in Example 1 was used as a copper precursor to create a copper film on a substrate. The substrate consisted of a silicon dioxide wafer with 250-Å layer of tantalum and a 100 Å layer of copper. The wafer had a barely discernable copper color.

Approximately 0.040 g of copper precursor was loaded in a dry box into a porcelain boat. The boat and wafer (~1 cm$^2$) were placed in a glass tube approximately 3.5 inches apart. The glass tube was removed from the dry box and attached to a vacuum line. Heating coils were attached to the glass tube surrounding both the area around the porcelain boat and the area around the wafer chip; this configuration allows the two areas to be maintained at different temperatures. Following evacuation of the system, an argon flow was created through the tube, passing first over the sample in the boat and then over the wafer. The pressure inside the tube was maintained at 150-200 mTorr. The region around the wafer was warmed to 110° C. After approximately an hour, the temperature of the region around the sample boat was raised to 55° C. These temperatures and the Ar gas flow were maintained for approximately 2.5 hours. The area around the sample boat was then cooled to room temperature. The tube was evacuated to a pressure of ~10 mTorr and was back-filled with diethylsilane. The area of the tube at 110° C. quickly turned a copper color. The apparatus was cooled and returned to the dry box. The copper color was perceptively darker. The process was repeated to yield a wafer with a smooth metallic copper film.

Example 3

Preparation of Pyridine(N,N'-diisopropyl-2,4-pentanediketiminate)copper

In the dry box, a 100-mL round-bottom flask was charged with $Cu(CH_3CN)_4SO_3CF_3$ (1.0 g, 2.65 mmol), pyridine (2.65 mmol), and ether (20 mL). In a separate 100-mL round-bottom flask, 1.7 M t-butyl lithium (1.56 mL) was added to a solution of N,N'-diisopropyl-2,4-pentanediketimine (2.65 mmol) and ether (20 mL). Both solutions were stirred for 25 min, after which the later solution was added to the former via pipette, which turned yellow then orange after uptake of all solids. The reaction mixture was stirred for 1.5 h before being concentrated under vacuum to a light orange solid. The crude solid was extracted with pentane (4×25 ml) and filtered. The filtrate was concentrated to give the desired product as a yellow powder (562 mg, 65%).

Example 4

Vinyltrimethylsilane(N-isobutyl,N'-methyl-2,4-pentanediketiminate)copper

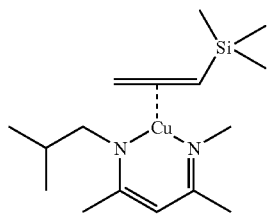

In a glove box, t-BuLi (0.861 mmol, 1.7 M in pentane) was added dropwise to a solution of N-isobutyl,N'-methyl-2,4-pentanediketimine (0.145 g, 0.861 mmol) in ether (10 mL) at room temperature. The resultant mixture was stirred at room temperature for 10 min. meanwhile, a mixture of [Cu(CH_3CN)_4]Tf (0.324 g, 0.861 mmol) and vinyltrimethylsilane (0.431 g, 4.307 mmol, 5 eq.) in ether (10 mL) was stirred at room temperature for 10 min. The diketiminate solution was added to the copper mixture, and then the resultant mixture was stirred at room temperature for 1 h. The solvent was stripped off under reduced pressure, and pentane (30 mL) was added to the residue. The mixture was filtered through Celite, and then the filtrate was concentrated under reduced pressure to afford 0.25 g (88% yield) of vinyltrimethylsilane(N-isobutyl,N'-methyl-2,4-pentanediketiminate)copper as a viscous liquid.

What is claimed is:

1. A process for forming copper deposits on a substrate comprising:

a. contacting a substrate with a copper complex, (I), to form a deposit of a copper complex on the substrate; and

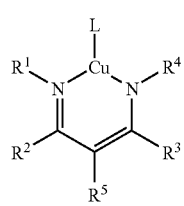

b. contacting the deposited copper complex with a reducing agent, wherein

L is selected from the group consisting of $C_2$-$C_{15}$ olefins, $C_2$-$C_{15}$ alkynes, and aromatic heterocycles;

$R^1$ and $R^4$ are the same and are selected from the group consisting of H, isobutyl, and neopentyl; or $R^1$ is isobutyl and $R^4$ is methyl, ethyl, isopropyl or neopentyl; or $R^1$ is neopentyl and $R^4$ is isopropyl;

$R^2$ and $R^3$ are independently methyl or ethyl;

$R^5$ is H; and the reducing agent is selected from the group consisting of 9-BBN (9-borabicyclo[3.3.1]nonane); diborane; boranes of the form $BR_xH_{3-x}$, where x=0, 1 or 2, and R is independently selected from the group consisting of phenyl and $C_1$-$C_{10}$ alkyl groups; dihydrobenzofuran; pyrazoline; disilane; silanes of the form $SiR'_yH_{4-y}$, where y=0, 1, 2 or 3, and R' is independently selected from the group consisting of phenyl and $C_1$-$C_{10}$ alkyl groups; and germanes of the form $GeR''_zH_{4-z}$, where z=0, 1, 2, or 3, and R'' is independently selected from the group consisting of phenyl and $C_1$-$C_{10}$ alkyl groups.

2. The process of claim 1, wherein L is vinyltrimethylsilane.

3. The process of claim 1, wherein the substrate is selected from the group consisting of copper, silicon wafers and silicon dioxide coated with a barrier layer.

4. The process of claim 1, wherein the substrate is exposed to a vapor of the copper complex.

5. The process of claim 1, wherein the deposition is carried out at 0 to 200° C.

6. The process of claim 1, wherein the reducing agent is silane or diethylsilane.

7. A copper complex, (I),

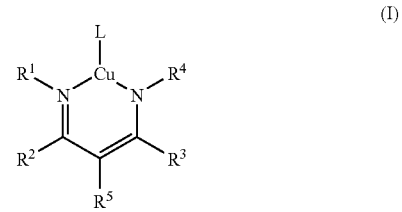

wherein

L is selected from the group consisting of $C_2$-$C_{15}$ olefins, $C_2$-$C_{15}$ alkynes, and aromatic heterocycles;

$R^1$ and $R^4$ are the same and are selected from the group consisting of H, isobutyl, and neopentyl; or $R^1$ is isobutyl and $R^4$ is methyl, ethyl, isopropyl or neopentyl; or $R^1$ is neopentyl and $R^4$ is isopropyl;

$R^2$ and $R^3$ are independently methyl or ethyl;

$R^5$ is H.

8. The copper complex of claim 7, wherein

L is vinyltrimethylsilane; $R^1$ and $R^4$ are iso-butyl; and $R^2$, $R^3$ are methyl and $R^5$ is H.

9. The copper complex of claim 7, wherein
L is vinyltrimethylsilane; $R^1$ and $R^4$ are H; and $R^2$, $R^3$ are methyl and $R^5$ is H.

10. An article produced by contacting a substrate with a copper complex of claim 7.

11. The article of claim 10, wherein the substrate is selected from the group consisting of copper, silicon wafers, and silicon dioxide coated with a barrier layer.

12. The article of claim 11, wherein the barrier layer is selected from the group consisting of tantalum, tantalum nitride, titanium, titanium nitride, tantalum silicon nitride, titanium silicon nitride, tantalum carbon nitride, and niobium nitride.

* * * * *